US005665392A

United States Patent [19]
Kumar et al.

[11] Patent Number: 5,665,392
[45] Date of Patent: Sep. 9, 1997

[54] FORMULATION FOR TREATING THALASSEMIA AND A PROCESS FOR PREPARING THE SAME

[75] Inventors: Sarkar Ajit Kumar; Kumar Sudarshan, both of New Delhi; Priyadarshi Harsh, Allahabad; Khanna Sushil Rattan; Dass Ghansham, both of Delhi, all of India

[73] Assignee: Council of Scientific and Industrial Research, New Delhi, India

[21] Appl. No.: 500,628

[22] Filed: Jul. 11, 1995

[51] Int. Cl.⁶ ..................................................... A61K 9/14
[52] U.S. Cl. ........................................ 424/489; 424/195.1
[58] Field of Search ................................. 424/489, 195.1

[56] References Cited

PUBLICATIONS

The Marshall Cavendish Illustrated Encyclopedia of Family Health; Thalassaemia; pp. 2373–2374.
Anemones, p. 114.
Clinical Trials of Deferiprone (L1), A.V. Foffbrand (Royal Free Hospital, pp. 2–3, Issue No. 61.
Desferal, p. 601.
C. Hershko, Iron–Chelating Therapy, vol. 26, Issue 4 (1988), pp. 303–345.

*Primary Examiner*—Jyothsna Venkat
*Attorney, Agent, or Firm*—Ladas & Parry

[57] ABSTRACT

A pharmaceutical formulation useful for treating patients suffering from thalassemia, which comprises powder of Anemonin Pretensis in an amount in the range of 0.02 to 0.12 wt % of the formulation, quinine sulphate in an amount in the range of 0.0005 to 0.003 wt % of the formulation, distilled or demineralised water in an amount in the range of 0 to 40 wt % of the formulation and, ethanol in an amount in the range of 99.88 to 60 wt % of the formulation; and a process for preparing the formulation by mixing the above ingredients.

10 Claims, 2 Drawing Sheets

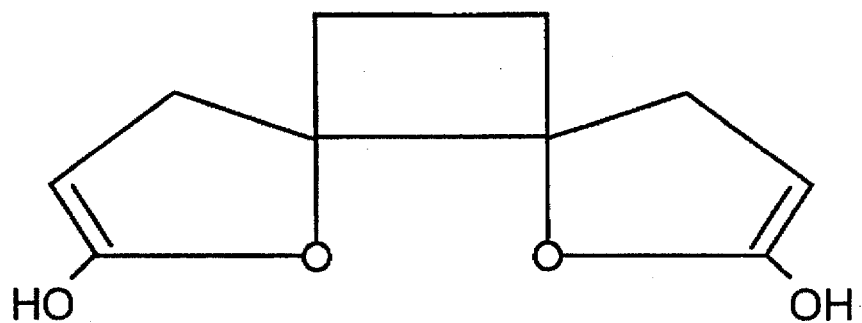
F I G. 1
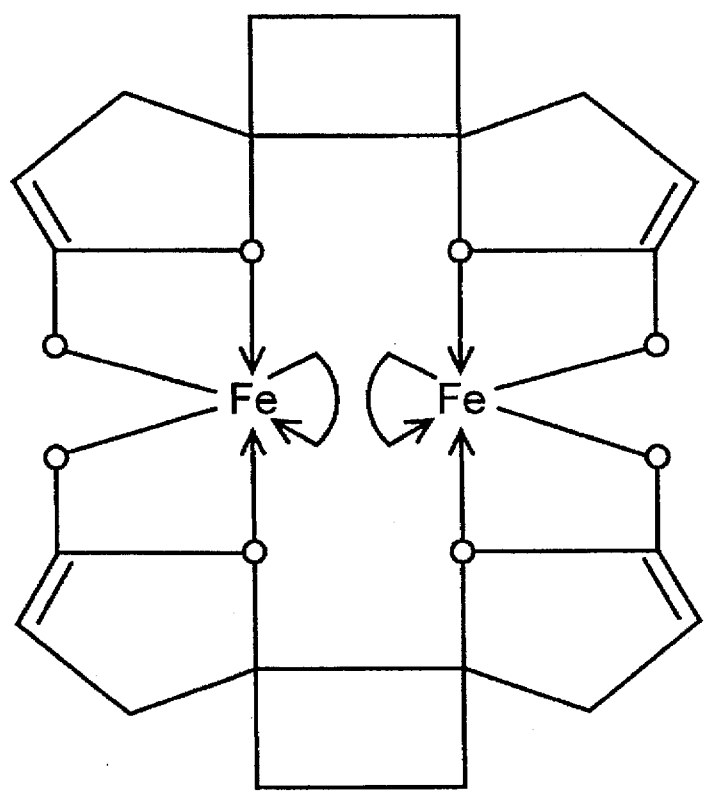
F I G. 2

FORMULATION FOR TREATING THALASSEMIA AND A PROCESS FOR PREPARING THE SAME

FIELD OF THE INVENTION

This invention relates to a formulation for iron-chelation. The formulation of the present invention is useful for treating patients suffering from the disease of Thalassemia.

This invention relates particularly to a formulation having increased therapeutic efficacy useful for the treatment of patients suffering from the disease of Thalassemia.

BACKGROUND OF THE INVENTION

Thalassemia is a dreaded disease among children. The disease is caused due to hereditary disorders connected with defective hemoglobin synthesis, characterised by hypochromia, microcytosis, haemolysis and a variable degree of anaemia. Thalassemia involves a heterogeneous group of molecular defects with a wide spectrum of clinical expressions.

Patients suffering from Thalassemia suffer from anaemias with decreased or absence of synthesis of a globin chain of a normal haemoglobin. The patients of thalassemia are broadly classified into two major groups according to the affected globin chain.

Alpha ($\alpha$) Thalassemia is associated with decreased or absence of $\alpha$-chain synthesis. Beta ($\beta$) Thalassemia is associated with decreased or absence of $\beta$-chain synthesis.

One may find also patients suffering from Thalassemia delta ($\delta$) and Gamma ($\gamma$) chain disorders, as well as those associated abnormal hemoglobin structure (e.g. Hb Lepose and Hb Constant Spring). These are rare and also contribute to the Thalassemia Syndromes.

The disease Thalassemia occurs world wide with a particular high incidence in the Mediterranean basin and in the South-East Asia. Malaria is also endemic in these areas—a significant fact since indirect evidence suggests that—Thalassemia (major) heteroxygosity confers protection against malaria.

The $\beta$-Thalassemia or Thalassemia major type of the disease comprises a heterogeneous group of disorders usually characterised by absence of ($\beta°$) or decreased ($\beta+$) globin synthesis.

The type of $\beta$-Thalassemia is also classified according to the severity of the anaemia. These clinical classifications serve to differentiate homozygous (Thalassemia intermedia or Thalassemia major) from heterozygous state (Thalassemia minima or Thalassemia minor). Though, it does not reflect genetic mutation, Thalassemia (minor) is a reduced rate of $\beta$-globin synthesis, with an increased $\alpha$-$\beta$ globin chains, but it is not like threatening.

Thalassemia (Major) also known as Cooley's anaemia, Mediterranean anaemia and Von-Jacksch's anaemia is characterised by marked anaemia (ranging from 1 to 6 gm/dl of homoglobin), severe hemolysis and ineffective erthropoiresis. The diagnosis is made in the 1st year of the life of the patient, often as early as 3 months. In the case of Thalassemia (Major), iron in the haemoglobin also breaks down and gets deposited in the vital organs of the body of the patients e.g. liver, kidney, spleen, heart etc. This is also known as iron overloading in the body and the life span of the child suffering from Thalassemia (major) becomes unpredictable. Every year out of 1,00,000 children born with Thalassemia (major) in the world, 10,000 are born in India.

The method which is available hitherto for the treatment of Thalassemia (major) is life long blood transfusions coupled with the taking of the drug called 'Desferal' daily intermusculary. The chemical name of the drug is Deferoxamine Methane Sulphonate and the chemical formula is $C_{28}H_{52}N_4O_{11}S$.

Desferal is administered by injection and leads to the excretion of iron from the body of the patient through urinary excretion. It was found by medical profession that Desferal had many side effects like swelling of limbs, stiffness in joints and may inhibit tumor cell proliferation, parasite growth and the proliferation of the cerebral Malarial Parasite, Plasmodium Faliparum.

In addition, the above drug is to be injected daily under the skin of the patient in a controlled manner in such a way to avoid any side reaction causing allergic conditions. Such a treatment is highly painful. The treatment is also costly as the vial containing 500 mg of dry active substance will cost about US $10/-each.

Through a new oral iron chelating drug known as L-1, CP20, DMPH, Deferiprone (Chemical Name, 1,2, Dimethyl 3 Hydroxypyridine 4-one) has been reported very recently, it is yet to establish its potentiality of patients suffering from the disease of Thalssemia. The reported side effects of this drug are 1. Myelotoxicity i.e. occurance of neutropenia 2. Orthropathy i.e. skeleto-muscular pain and swelling around knee and hipjoints and lastly mild zinc defficiency occasionally leading to dermatopathy. (Reference may be made to the Proceedings of National Thalassemia Conference, 5–6 Feb., 1994, held in Delhi; L1: Oral Iron chelation Therapy-Indian Study by M. B. Agarwal). The cost of a capsule Deferiprone is approximately 50 U.S. cents (Rs. 12/-). A patient has to take 3–6 capsules per day. This will amount to US $70–90 (Rs. 1000–2000) per month.

Another method which is available for the treatment of the disease Thalassemia (major) is by the bone marrow transplantation (BMT). This is done by the taking the bone marrow of the matching donor and injecting it to the patient. The cost of such a treatment is around US $50000/-(Rs. 15,00,000/-). This is therefore beyond the reach of common man. Several treatments using bone marrow have been performed in many parts of the world including the U.S.A. and Italy. Recently, Christian Medical Colleage (Vellore), India and Appolo Hospital (Madras) India have also started this type of BMT treatment in India, but the cost is also on the higher side (Rs. 7 Lac. approx). Further, an increase in the life expectancy of these patients has yet to be established.

Under the prevailing present day conditions, regular blood transfusion and use of the drug 'Desferal' by injection as explained above, is the best way to this dreaded disease. For the last decade, efforts are being made by medical profession throughout the world to find a treatment of this disease by a drug which will be low in cost and can be administered orally and have no side effects, but so far there has been no success.

SUMMARY OF THE INVENTION

Therefore, the main objective of the present invention is to provide a formulation useful for iron-chelation for the treatment of Thalassemia.

Another objective of the present invention is to provide a formulation useful for the treatment of Thalssemia with increased therapeutic efficacy.

Yet another objective of the present invention is to provide a formulation for the treatment of Thalassemia which is much cheaper and hence affordable by a common man.

Still, another objective of the present invention is to provide a formulation useful for the treatment of patients suffering from Thalassemia which can be administered orally.

A further objective of the present invention is to provide a formulation which has no side effects and is very convenient to administer.

Another object of the present invention is to provide a formulation useful for the treatment of Thalassemia, the dose of which can be continued for a long period without damaging any vital organs body of the patients.

BRIEF DESCRIPTION OF THE DRAWINGS

FIG. 1 shows the formula of anemonin pretensis.

FIG. 2 shows the structure of the iron-anemonin complex

DETAILED DESCRIPTION OF THE INVENTION

Figure 3:
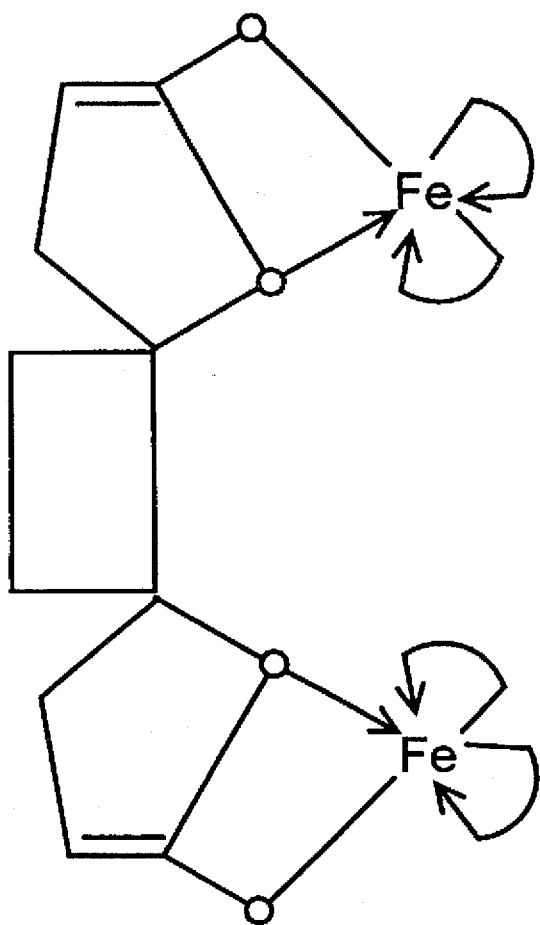
FIG. 3 shows the structure of the iron -anemonin complex (stretched)

With the above objectives in view, our work was directed to red blood cells and at the same time, to enhance the oxygen carrying capacity to the tissues. Different compounds of Vanadium, Arsenic, oxalic acid and citric acid were tried initially but these compound failed in making a major break through.

It has been observed that patients suffering from Thalassemic disease have a change in complexion, anorexia, blackness of gums, increase in serum ferretin level and a remarkable iron overload in the body due to the breaking down of red blood cells. The treatment mentioned above which involves repeated blood transfusion also accumulates the above elements in the body of the patients suffering from Thalassemic disease.

Children suffering from Thallassemia disease do not show any resistance from viral infection and also suffer from body aches. They are also immune to malaria.

Our research work was primarily directed to find an immediate solution for the survival of such patients, who had an iron overload in the body and the other side ailments mentioned above.

Efforts, therefore, were directed towards finding out an alternate drug which can be used orally and have no side effects. Anemonin Pretensis (powder) has been used for many years by the tribal people of Siberia to poison their arrows. Anemonin Pretensis is extracted with an organic solvent such as ethanol from fresh whole wind flower plant (the botanical name by Anemonin) with roots and flowers and some fruits of wind flowers. The dried material is treated with an organic solvent such as ethanol and refluxed. Anemonin Pretensis obtained from the extraction is filtered and recrystrallized from an organic solvent such as ethanol. The medical history of this herb also reveals that this herb was involved in homeopathic practice in 1805 for some female hormone problem.

Anemonin Pretensis is a pure herbal product. It is present in the wind flower plant which grows in the wild state in the open fields and plains in many parts of Europe, Russia and Turkey in Asia. The chemical formula of Anemonin pretensis having the formula 1, shown in the drawing accompanying this specification, isolated from fresh wind flower plant is 1-2 dihydroxy 1-2 cyclobutane diacrylic acid di-lactone. Reference may be made to Merck index P-87, Entry no. 677, 9th edition.

Patients suffering from Thallassemic disease are immune to malaria. Considering the nature and considering that quinine sulphate is a known antimalarial drug which has antipyretic and analgesic properties, we considered incorporating quinine sulphate in the formulation to reduce the high temperature and body-ache problem of the patients suffering from Thalassemic disease.

Quinine has the chemical composition $C_{20}H_{24}N_2O_2$. It is obtained from Cinchona bark available in India, Sri Lanka, Equador, Columbia, Peru and Bolivia. Cinchona thrives at higher elevations such as 6000–8500 ft. Quinine is also extracted with an organic solvent such as ethanol from the bark of the plant (Cinchone), refluxed, filtered and recrystallized with an organic solvent such as ethanol. Quinine sulphate is prepared by reacting quinine and dilute sulphuric acid in a (2:1) molar ratio as shown below:

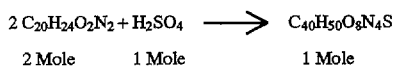

$$2\ C_{20}H_{24}O_2N_2 + H_2SO_4 \longrightarrow C_{40}H_{50}O_8N_4S$$

2 Mole    1 Mole    1 Mole

Quinine Sulphate can be in the form of crystallized needles and is snow white, light odorless, and extremely bitter and the chemical composition $C_{40}H_{48}N_4O_4$, $H_2SO_4$ & $H_2O$. Reference may be made to Merck Index p-1049, entry no. 7879, 9th edition.

By our continuous and sustained research work based on the above mentioned directions, we observed that when we blended (preferable mechanically) the powder of Anemonin Pretensis with quinine sulphate and dissolved in suitable solvent and the solution was administered orally to the patient suffering from Thalassemia, there was remarkable improvement of complexion and reduction of serum ferritin level. There was no fever. There was also no body ache. The treatment was continued and more patients were put on trial on this drug. There were no side effects. This revealed that the formulation is very useful in the treatment of the patients suffering from Thallassemia.

Accordingly, the present invention provides a pharmaceutical formulation useful for treating patients suffering from thalassemia which comprises:

i. Powder of Anemonin Pretensis in an amount in the range of 0.02 to 0.12 wt % of the formulation.

ii. Quinine sulphate in an amount in the range of 0.0005 to 0.003 wt % of the formulation.

iii. Distilled or demineralised water in an amount in the range of 0 to 40 wt % of the formulation, and iv. Edible solvent 99.88 to 60 wt % of the formulation.

The solvent used may be selected from solvent ethanol, absolute alcohol etc.

The solvent may be present in an amount of 89.9795 wt %, 89.9592 wt %, 89.939 wt %, 89.918 wt %, 89.97 wt %, 89.95 wt %, 88.87 wt %, 89.92 wt %, 89.94 wt %, 19.909 wt % or 59.919 wt %.

The anemonin pretensis powder and the quinine sulphate employed in the formulation may be of pharmaceutical grade.

The Anemonin Pretensis posseses the properties of chelating iron. Quinine sulphate seems to accelerate the chelation of iron present in the body of the patient suffering from thalassemia. We have found by forming a formulation of Anemonin Pretensis and Quinine sulphate in the amount mentioned above results in an unexpected properties which are not present in the individual components. There is, therefore, a synergistic activity when they are combined in the above mentioned quantities.

The formulation of the present invention is therefore, not a mere admixture of the ingredients employed but a synergistic mixture, the properties of which are not merely the aggregate properties of the individual ingredients of the formulation.

The formulation of the present invention when administered to patients suffering from Thalassemic disease works as follows:

The iron present in the body of the patients forms a complex with anemonin shown in formula 2 of the drawings (closed ring structure) or in formula 3 of the drawings (stretched structure) where three molecules of anemonin can form a complex with two iron atoms. The quinine sulphate present in the formulation acts as a catalyst for the formation of the complex thereby not only reducing the amount of Anemonin in the complex/composition but also using the maximum amount of iron present in the body. In addition, the antipyretic and analgesic properties of quinine sulphate help to control the fever and the body ache problem present in such patients.

The iron complex is formed in the body fluids. The fluid containing the complex reaches the kidney and it is then excreted from the body of patients through urine. Some of the complex is also excreted through alimentary canal and finally feces. By these processes the excess iron present in the body of the patients is removed thereby enhancing the life span of the patients. The various ingredients of the present formulation can be blended by any conventional methods such as mechanically mixing etc.

The following examples are given by way of illustration and these should not be construed to limit the scope of the present invention.

EXAMPLE 1

A formulation was prepared by blending the following ingredients:

| Powder of Anemonin Pretensis | 0.02 wt % of the formulation |
| --- | --- |
| Quinine Sulphate | 0.0005 wt % of the formulation |
| Demineralised Water | 10 wt % of the formulation |
| Ethanol Solvent | 89.9795 wt % of the formulation |

EXAMPLE 2

A formulation was prepared by blending the following ingredients:

| Powder of Anemonin Pretensis | 0.04 wt % of the formulation |
| --- | --- |
| Quinine Sulphate | 0.0008 wt % of the formulation |
| Demineralised Water | 10 wt % of the formulation |
| Ethanol Solvent | 89.9592 wt % of the formulation |

EXAMPLE 3

A formulation was prepared by blending the following ingredients:

| Powder of Anemonin Pretensis | 0.06 wt % of the formulation |
| --- | --- |
| Quinine Sulphate | 0.001 wt % of the formulation |
| Demineralised Water | 10 wt % of the formulation |
| Ethanol Solvent | 89.939 wt % of the formulation |

EXAMPLE 4

A formulation was prepared by blending the following ingredients:

| Powder of Anemonin Pretensis | 0.08 wt % of the formulation |
| --- | --- |
| Quinine Sulphate | 0.002 wt % of the formulation |
| Demineralised Water | 10 wt % of the formulation |
| Ethanol Solvent | 89.918 wt % of the formulation |

EXAMPLE 5

A formulation was prepared by blending the following ingredients:

| Powder of Anemonin Pretensis | 0.09 wt % of the formulation |
| --- | --- |
| Quinine Sulphate | 0.001 wt % of the formulation |
| Demineralised Water | 10 wt % of the formulation |
| Ethanol Solvent | 89.919 wt % of the formulation |

EXAMPLE 6

A formulation was prepared by blending the following ingredients:

| Powder of Anemonin Pretensis | 0.12 wt % of the formulation |
| --- | --- |
| Quinine Sulphate | 0.003 wt % of the formulation |
| Demineralised Water | 10 wt % of the formulation |
| Ethanol Solvent | 88.8779 wt % of the formulation |

EXAMPLE 7

A formulation was prepared by blending the following ingredients:

| Powder of Anemonin Pretensis | 0.09 wt % of the formulation |
| --- | --- |
| Quinine Sulphate | 0.001 wt % of the formulation |
| Demineralised Water | 80 wt % of the formulation |
| Ethanol Solvent | 19.909 wt % of the formulation |

EXAMPLE 8

A formulation was prepared by blending the following ingredients:

| Powder of Anemonin Pretensis | 0.08 wt % of the formulation |
| --- | --- |
| Quinine Sulphate | 0.001 wt % of the formulation |
| Demineralised Water | 40 wt % of the formulation |
| Ethanol Solvent | 59.919 wt % of the formulation |

The formulations mentioned in Examples 1 to 8 were administered to patients of different age groups who were suffering from Thalassemia. The patients were administered the above formulation orally after mixing it with water. The formulation was administered to the patient daily. Such a treatment was continued for a period of two months. All the formulations showed that iron is excreted in urine after the administration of the formulation at a range from 10–95 %. This result points out that the formulation of the present invention is very effective for the chelation of iron, thereby reducing the serum ferritine level in the patients suffering from Thalassemia. Such a position results in longer and larger survival rate of the patients suffering from Thalassemia. The above mentioned results are shown in Table 1.

TABLE 1

Efficiency of the formulation of the present invention.

| Formulation used | No. of patient treated | Age (yrs) | Sex | Frequency of transfusion (days) | Duration of treatment (months) | Medicine Administered in drops twice daily | Excretion chelated iron (%) |
|---|---|---|---|---|---|---|---|
| Example 1 | 3 | 5 | M | 22 | 2 | 15 | 15 |
|  |  | 7 | F |  |  |  | 25 |
|  |  | 7 | F |  |  |  | 25 |
| Example 2 | 3 | 9 | M | 20 | 2 | 15 | 40 |
|  |  | 9 | M |  |  |  | 25 |
|  |  | 11 | M |  |  |  | 30 |
| Example 3 | 3 | 7 | M | 21 | 2 | 15 | 40 |
|  |  | 7 | M |  |  |  | 40 |
|  |  | 9 | F |  |  |  | 50 |
| Example 4 | 3 | 15 | M | 20 | 2 | 15 | 70 |
|  |  | 20 | F |  |  |  | 70 |
|  |  | 23 | F |  |  |  | 80 |
| Example 5 | 3 | 3 | M | 21 | 2 | 15 | 90 |
|  |  | 9 | F |  |  |  | 91 |
|  |  | 19 | M |  |  |  | 95 |
| Example 6 | 3 | 10 | M | 22 | 2 | 15 | 20 |
|  |  | 11 | F |  |  |  | 20 |
|  |  | 12 | M |  |  |  | 30 |
| Example 7 | 3 | 15 | M | 21 | 2 | 15 | 10 |
|  |  | 16 | F |  |  |  | 15 |
|  |  | 19 | F |  |  |  | 10 |
| Example 8 | 3 | 7 | M | 20 | 2 | 15 | 75 |
|  |  | 9 | M |  |  |  | 75 |
|  |  | 11 | F |  |  |  | 80 |

TABLE 2

Comparison of Desferal, Defriprone and the formulation of the present invention

| Name of the medicine | Mode of Administration | Side effects | Taste |
|---|---|---|---|
| Desferal | Injection (highly painful) | Adverse side effects such as:- <br> a. ocular toxicity <br> b. auditory meaurotoxicity <br> c. cerebral toxicity <br> d. allergic skin reaction <br> e. cardiovascular and gastro-intestinal disturbances <br> f. change in blood pressure | Does not apply |
| Defriprone | Oral | More side effects than Desferal such as:- <br> a. Myelotoxicity <br> b. Arthropathy <br> c. Mild Zine defficiency <br> d. Questionable occurance of immunological complications | Bitter taste |
| Formulation of the present invention | Oral | No side effects | Tasteless |

From the above table 2, it is clear that, the formulation of the present invention is easy to administer because it is tasteless, colorless and odorless with no side effects even when administered for longer periods.

TABLE 3

Annual cost of treatment of Thalassemia using the hitherto know drugs and the formulation of the present invention.

| Name of medicine | Amount in US $ | Reference |
|---|---|---|
| DESFERAL | 3000–6000 | Iron Chelation Therapy C. Hershko & D. J. Weatherall CRC Critical Reviews Clinical Laboratory Series 26(4), 314, 1988 |
| DEFRIPRONE (L-1) | 800–1100 | News Review, United Kingdom Thalassemia Soc Issue No. 61, March, 95 |
| PRESENT FORMULATION | 50–60 | — |

Table 3 illustrates that the cost of the present formulation is the cheapest when compared with known drugs.

The formulation of the present invention can be in the form of tablets, powder or suspension.

The main advantages of the formulation of the present invention are:

1. Iron-chelation using the formulation of Anemonin Pretensis and Quinine sulphate is up to 90 %.
2. The cost of the formulation is around US $5 to 10/-(Rs. 150–200/-) per 30 ml vial and it can be used for one month. The cost is much lower as compared to other currently available medicines in the market for the treatment of Thalassemia.
3. The formulation has no toxic effects even when it is administered for longer period.
4. The formulation is tasteless and odorless and can be administered orally.

We claim:

1. A pharmaceutical formulation for treating patients suffering from thalassemia which comprises:
   a. powder of Anemonin Pretensis in an amount in the range of 0.02 to 0.12 wt % of the formulation,
   b. quinine sulphate in an amount in the range of 0.0005 to 0.003 wt % of the formulation,
   c. distilled or demineralized water in an amount in the range of 0 to 40 wt % of the formulation and
   d. ethanol in an amount in the range of 99.88 to 60 wt % of the formulation.

2. A pharmaceutical formulation as claimed in claim 1, wherein the Anemonin Pretensis is present in an amount selected from the group consisting of 0.04 wt %, 0.06 wt %, 0.08 wt % and 0.09 wt % of the formulation.

3. A pharmaceutical formulation as claimed in claim 1, wherein the Anemonin Pretensis used is of pharmaceutical grade.

4. A pharmaceutical formulation as claimed in claim 1, wherein quinine sulphate used is of pharmaceutical grade.

5. A pharmaceutical formulation as claimed in claim 1, wherein the quinine sulphate is present in an amount selected from the group consisting of 0.0008 wt %, 0.001 wt %, and 0.002 wt % of the formulation.

6. A pharmaceutical formulation as claimed in claim 1, wherein the ethanol is present in an amount which is selected from the group consisting of 89.9795 wt %, 89.9592 wt %, 89.939 wt %, 89.918 wt %, 89.919 wt %, 89.97 wt %, 89.95 wt %, 88.87 wt %, 89.92 wt %, and 89.94 wt % of the formulation.

7. A process for the preparation of a pharmaceutical composition for treating patients suffering from Thalassemia, said process comprising mixing:
   a. powder of Anemonin Pretensis in an amount in the range of 0.02 to 0.12 wt % of the formulation,
   b. quinine sulphate in an amount in the range of 0.0005 to 0.003 wt % of the formulation,
   c. distilled or demineralized water in an amount in the range of 0 to 40 wt % of the formulation, and
   d. ethanol in an amount in the range of 99.8 to 60 wt % of the formulation.

8. A process as claimed in claim 7 wherein the anemonin pretensis powder and the quinine sulphate used are of pharmaceutical grade.

9. A pharmaceutical formulation for treating patients suffering from thalassemia which comprises:
   a. Powder of Anemonin Pretensis in an amount of 0.08 wt % of the formulation,
   b. Quinine sulphate in an amount 0.001 wt % of the formulation,
   c. Water in an amount of 40 wt %, and
   d. Ethanol is an amount of 59.919 wt % of the formulation.

10. A pharmaceutical formulation for treating patients suffering from thalassemia which comprises:
    a. Powder of Anemonin Pretensis in an amount of 0.09 wt % of the formulation,
    b. Quinine sulphate in an amount 0.001 wt % of the formulation,
    c. Water in an amount 80 wt % of the formulation and
    d. Ethanol in an amount of 19.909 wt % of the formulation.

* * * * *